US007926735B1

(12) United States Patent
Mobley

(10) Patent No.: US 7,926,735 B1
(45) Date of Patent: Apr. 19, 2011

(54) FRAGRANCE PACKAGE, DISPENSER, AND METHOD

(76) Inventor: David D. Mobley, Keller, TX (US)

( * ) Notice: Subject to any disclaimer, the term of this patent is extended or adjusted under 35 U.S.C. 154(b) by 0 days.

(21) Appl. No.: 12/208,474

(22) Filed: Sep. 11, 2008

Related U.S. Application Data

(63) Continuation-in-part of application No. 12/044,985, filed on Mar. 9, 2008, now abandoned.

(51) Int. Cl.
*A61L 9/04* (2006.01)

(52) U.S. Cl. .................. 239/53; 239/6; 239/34; 239/55; 239/42; 239/43; 239/60; 239/57; 206/494; 206/484; 206/449; 428/34.2; 428/34.3; 428/35.2; 428/905

(58) Field of Classification Search ................ 239/6, 34, 239/42, 43, 36, 51.5, 47, 55, 56, 59, 60, 57
See application file for complete search history.

(56) References Cited

U.S. PATENT DOCUMENTS

| | | | |
|---|---|---|---|
| 2,111,025 A * | 3/1938 | Galler .............................. 239/44 |
| 2,615,754 A | 3/1949 | Lindenberg |
| 2,720,419 A * | 10/1955 | Eby ................................ 239/54 |
| 2,757,957 A * | 8/1956 | Samann ........................ 239/53 |
| 3,065,915 A * | 11/1962 | Samann ........................ 239/35 |
| 3,819,043 A * | 6/1974 | Harrison ....................... 206/449 |
| 4,145,001 A | 3/1979 | Weyenberg et al. |
| 4,158,440 A | 6/1979 | Sullivan et al. |
| 4,283,011 A | 8/1981 | Spector |
| 4,458,810 A * | 7/1984 | Mahoney ....................... 206/210 |
| 4,739,879 A * | 4/1988 | Nakamura ..................... 206/205 |
| 5,087,273 A * | 2/1992 | Ward ................................ 96/147 |
| D394,605 S * | 5/1998 | Skiba et al. .................... D9/709 |
| 5,845,847 A | 12/1998 | Martin et al. |
| 6,164,441 A * | 12/2000 | Guy et al. ...................... 206/210 |
| 6,554,887 B1 * | 4/2003 | Inglis .............................. 96/222 |
| D487,224 S * | 3/2004 | Coonan .......................... D9/707 |
| 6,746,743 B2 * | 6/2004 | Knoerzer et al. ............. 428/42.1 |
| RE39,905 E | 11/2007 | Mobley |
| 2002/0182359 A1 * | 12/2002 | Muir et al. .................... 428/40.1 |
| 2005/0145711 A1 * | 7/2005 | Blondeau et al. ............... 239/60 |
| 2006/0018569 A1 * | 1/2006 | Bonenfant ........................ 383/5 |
| 2008/0223939 A1 * | 9/2008 | Halbur et al. .................. 235/494 |

* cited by examiner

*Primary Examiner* — Dinh Q Nguyen
*Assistant Examiner* — Trevor E McGraw
(74) *Attorney, Agent, or Firm* — Dan Brown Law Office; Daniel R. Brown

(57) ABSTRACT

An apparatus for dispersing a fragrance compound. The apparatus includes a fragrance compound impregnated porous carrier with a film wrapped there about to form an envelope hermetically sealed along at least a first seam in the film. The film is perforated with at least a first slit to define a vent opening removable portion retained to the envelope with at least a first tab of film bridging the first slit. A film vent closure is adhesively applied to the envelope about the vent opening removable portion, thereby forming a substantially complete hermetic seal of the interior of the envelope about the porous carrier. Upon removal, the film vent closure adhesively pulls the vent opening removable portion from the envelope, and the first tab of film is torn, so as to form a vent opening in the envelope, and thereby enabling the fragrance compound to disperse through the vent opening.

18 Claims, 8 Drawing Sheets

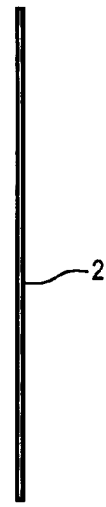
Fig. 4A
Fig. 4B
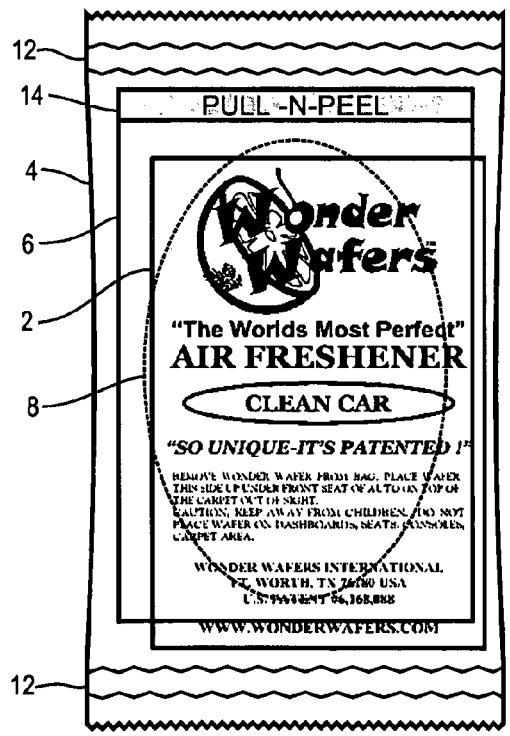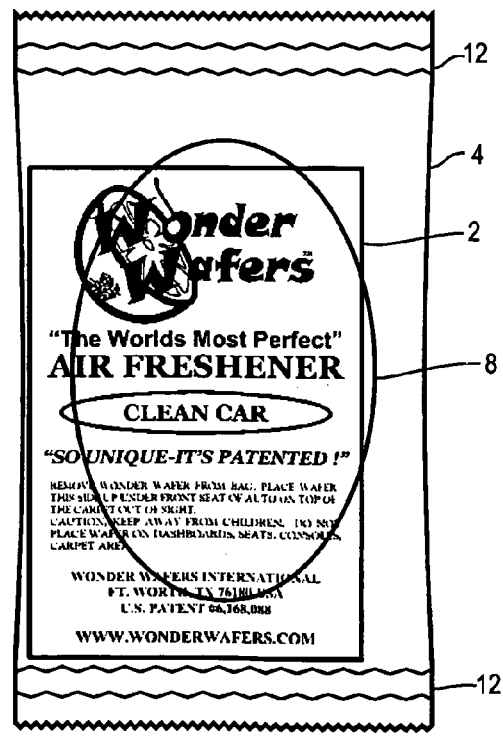
Fig. 5
Fig. 6

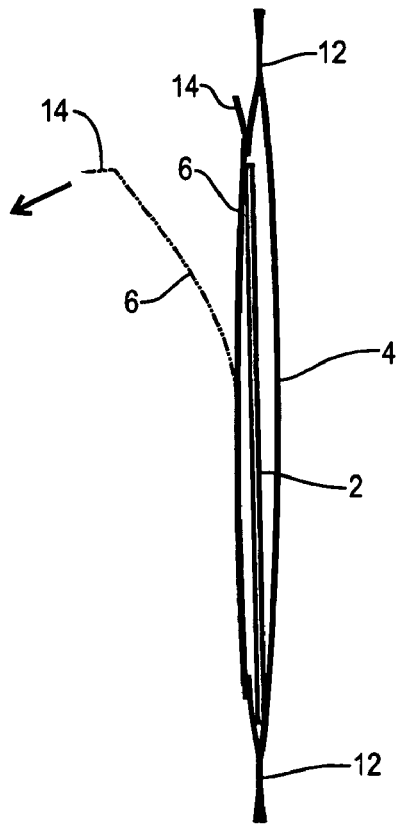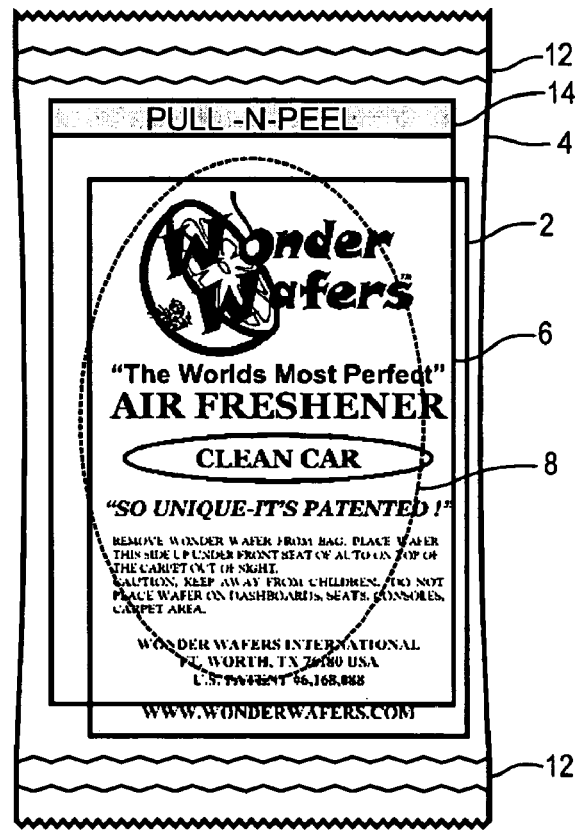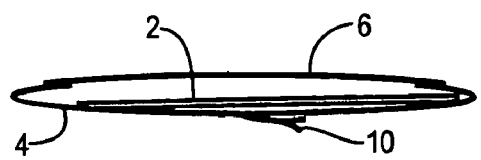
**Fig. 7B
Section**
Fig. 7A
**Fig. 7C
Section**

Section A

Section B

Section C

Section D

FRAGRANCE PACKAGE, DISPENSER, AND METHOD

BACKGROUND OF THE INVENTION

1. Field of the Invention

The present invention relates to methods of manufacture and apparatus for dispersing fragrance compounds. More specifically, the present invention relates to a fragrance compound impregnated porous carrier enclosed within a hermetically sealed envelope with a removable vent closure, which enables the fragrance compounds to disperse through the vent opening.

2. Description of the Related Art

Fragrance compounds are produced and used to disperse fragrances into the air within an ambient environment. The dispersed fragrances serve the purposes of presenting pleasurable aromas, freshening the air, concealing objectionable odors, and providing certain therapeutic benefits. Fragrance compounds are comprised of one or more fragrance components and one or more fragrance carrier solutions. The fragrance components combine to produce the desired aroma, such as lemon, cherry, vanilla, and so forth. Individual fragrances typically include from eight to over thirty fragrance components. These components may include fragrance oils, esters, glycols, alcohols, acetate, and so forth. Manufacturers often keep the specific fragrance formulations secret because of the subjective artistic nature of fragrance development and formulation. Fragrance carrier solutions are used to aid in the vaporization and dispersion of the fragrance components into the air. Various carrier solutions are known, and may include water, alcohols, di-propylene glycol, diethyl phthalate, hexylene glycol, and so forth. The ratio and mixtures of fragrance components and fragrance carriers are also quite specific, depending on the desired intensity of the fragrance, the duration of the dispersion period, other application factors and so forth. Fragrance compound formulations are also commonly held in confidence by fragrance producers.

Once a fragrance compound has been designed and produced, it then must be packaged, delivered, stored and ultimately be dispersed into an ambient environment. One type of packaging is a sealed bottle of a liquid fragrance compound. However, this type of product delivery does not lend itself well to consumer level consumption. The problem is that a bottle of liquid does not include any convenient means for later dispersion of the fragrance at the end user level. A more user-friendly approach is to permeate the fragrance compound into physical structure that enables the vaporization and dispersion of the fragrance compound into the air. An example of such a system is disclosed in U.S. Reissue Pat. No. Re39,905 to Mobley for AIR FRESHENER CARD, METHOD OF USE AND METHOD OF MANUFACTURE, the contents of which are hereby incorporated by reference. Mobley is also the inventor of the presently disclosed invention. The U.S. Pat. No. Re39,905 disclosure employs a cardboard card impregnated with air freshener as the physical carrier of the fragrance compound to aid in dispersion of the fragrance by the end user. The cards are impregnated and then stored in a hermetically sealed container until they are deployed into service.

The most likely end user of the air freshener cards of the Mobley U.S. Pat. No. Re39,905 disclosure are individuals involved in the automotive services industries, a car wash employee, for example, who retrieve a card out of the hermetically sealed container and places it under the seat of an automobile. This action exposed the card to the air, where the fragrance compound can begin vaporization and dispersion. The hermetically sealed container is a plastic canister with an airtight lid that contains hundreds of fragrance cards. Each cardboard card has the brand name, manufacturer, and instructions for use printed thereon. Each card is damp with a specific quantity of fragrance compound when it is withdrawn from the container. The problem with this approach is that the card must ultimately rest on some surface, and that surface is then in physical contact with the damp fragrance compound, which can stain, discolor, and otherwise affect the surface. Similarly, the car wash employee must touch the card when it is retrieved, and thusly comes into contact with the fragrance compound. Of course, in the case of a car wash application, the hidden location of the resting surface obviates the problem of physical contact, and the car wash employee can be provided gloves to protect his fingers, or otherwise instructed in safe handling procedures for the cards.

There is also a consumer market for the aforementioned fragrance cards. This market differs substantially from the car wash market in that the consumer typically does not want to purchase a plastic canister of fragrance cards containing hundreds of cards. Rather, the consumer desires a much smaller number of cards, perhaps as few as just one card at a time. The cost of individual plastic canisters is prohibitive, so the cards are packaged into cellophane sleeves and sold individually, or in packages containing a small number of individually wrapped cards. The cellophane sleeve provides the hermetically sealed environment that contains the card and fragrance compound until the consumer tears open the cellophane to retrieve the card and places it into service. However, the aforementioned problems of human contact with the fragrance compound and contact with the surface on which the card ultimately rests are not addressed by the individually wrapped consumer product. These limitations greatly constrict the market range for such products. Thusly, it can be appreciated that there is a need in the art for an apparatus and method of manufacture for a fragrance delivery product that disperses a fragrance compound while simultaneously addressing the problems in the art, and at a sufficiently low price point so as to be both desirable to consumers and profitable to manufacturers and retailers.

SUMMARY OF THE INVENTION

The need in the art is addressed by apparatus and methods of the present invention. The present invention teach an apparatus for dispersing a fragrance compound. The apparatus includes a fragrance compound impregnated porous carrier with a film wrapped there about to form an envelope hermetically sealed along at least a first seam in the film. The film is perforated with at least a first slit to define a vent opening removable portion retained to the envelope with at least a first tab of film bridging the first slit. A film vent closure is adhesively applied to the envelope about the vent opening removable portion, thereby forming a substantially complete hermetic seal of the interior of the envelope about the porous carrier. Upon removal, the film vent closure adhesively pulls the vent opening removable portion from the envelope, and the first tab of film is torn, so as to form a vent opening in the envelope, and thereby enabling the fragrance compound to disperse through the vent opening.

In a specific embodiment of the foregoing apparatus, the film is impervious to the fragrance compound. In another specific embodiment, the porous carrier has information imprinted thereon, and, the film wrapped to form the envelop is transparent, which facilitates visual access to the information imprinted on the porous carrier. In another specific embodiment where the porous carrier has information imprinted thereon, the film vent closure is transparent, which facilitates visual access to the information imprinted on the porous carrier. In specific embodiments of the apparatus, the film envelope and the film vent closure are polyester. In another specific embodiment, the vent opening size and shape are selected to retain the porous carrier within the envelope regardless of where the porous carrier may be positioned within the envelope.

In a specific embodiment of the foregoing apparatus, the film is perforated with plural slits to define the vent opening removable portion, which is then retained to the envelope with plural tabs of film bridging the plural slits. In another specific embodiment, the film is perforated with plural slits to define plural vent opening removable portions, which are retained to the envelope with corresponding plural tabs of film.

In a specific embodiment of the foregoing apparatus, the porous carrier is a paperboard card. In another specific embodiment, the film vent closure includes a portion accessible for manual removal thereof from the envelope. In a refinement to this embodiment, portion accessible for manual removal is a pull tab that is not adhered to the envelope. In another embodiment of the apparatus, the film vent closure is adhesively applied to the envelope with a resealable tacky adhesive. In another embodiment, the film wrapped about the porous carrier to form the envelope is hermetically sealed along a spine seam, a first end seam and a second end seam.

The present invention teaches a method of manufacturing an apparatus for dispersing a fragrance compound. The method includes the step of impregnating a porous carrier with a fragrance compound. Then, perforating a film with at least a first slit defining a vent opening removable portion retained with at least a first tab of film bridging the slit, and then wrapping the film about the porous carrier, forming an envelope there about. It also includes hermetically sealing the envelope along at least a first seam in the film, and adhesively applying a film vent closure to the envelope about the vent opening removable portion, thereby forming a substantially complete hermetic seal of the interior of the envelope about the porous carrier. Then, removing the film vent closure, thereby adhesively pulling the vent opening removable portion from the envelope and tearing the first tab of film, and thereby forming a vent opening in the envelope. This then enables the dispersing the fragrance compound through the vent opening.

In a specific embodiment, the foregoing method includes the further step of imprinting information onto the porous carrier. In another embodiment, the film that forms the envelope is transparent, thereby facilitating visual access to the information imprinted on the porous carrier. In another embodiment, the film vent closure is transparent, thereby facilitating visual access to the information imprinted on the porous carrier.

In a specific embodiment, the foregoing method includes the further steps of perforating the film with plural slits, thereby retaining the vent opening removable portion with plural tabs of film. I another embodiment, the method includes the further steps of perforating the film with plural slits, thereby defining plural vent opening removable portions retained to the envelope with corresponding plural tabs of film. In another embodiment, the method includes the further steps of hermetically sealing the envelope along a spine seam, a first end seam and a second end seam.

BRIEF DESCRIPTION OF THE DRAWINGS

FIGS. 4A and 4B are drawings of a fragrance impregnated wafer according to an illustrative embodiment of the present invention.

FIG. 5 is a drawing of a packaged fragrance impregnated wafer according to an illustrative embodiment of the present invention.

FIG. 6 is a drawing of a packaged fragrance impregnated wafer placed in use according to an illustrative embodiment of the present invention.

FIGS. 7A, 7B, and 7C are drawings of a packaged fragrance impregnated wafer according to an illustrative embodiment of the present invention.

DESCRIPTION OF THE INVENTION

Figure 1:
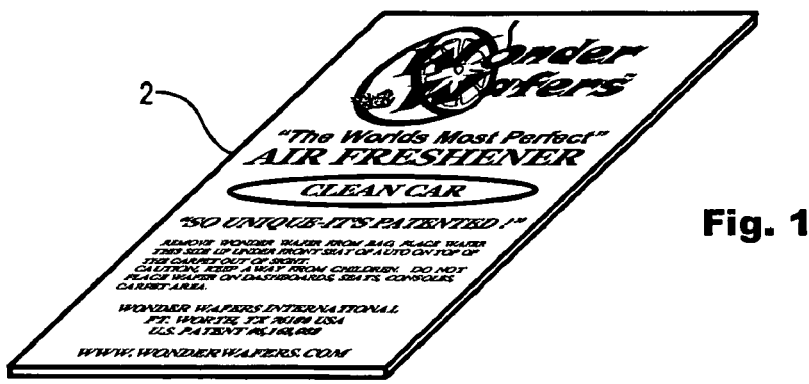
FIG. 1 is a drawing of a fragrance impregnated wafer according to an illustrative embodiment of the present invention.

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto.

Those having ordinary skill in the art and access to the teachings provided herein will recognize additional modifications, applications, and embodiments within the scope hereof and additional fields in which the present invention would be of significant utility.

In considering the detailed embodiments of the present invention, it will be observed that the present invention resides primarily in combinations of steps to accomplish various methods and components to form various apparatus. Accordingly, the apparatus components and method steps have been represented where appropriate by conventional symbols in the drawings, showing only those specific details that are pertinent to understanding the present invention so as not to obscure the disclosure with details that will be readily apparent to those of ordinary skill in the art having the benefit of the disclosures contained herein.

In this disclosure, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a" does not, without more constraints, preclude the existence of additional identical elements in the process, method, article, or apparatus that comprises the element.

The present invention advances the art by teaching a method of manufacture and a fragrance delivery product useful for dispersing a fragrance compound. In the illustrative embodiment, a fragrance compound impregnated paperboard card has manufacturer and usage instructions imprinted thereon, and is wrapped with an impermeable film to form an envelope. At least a portion of the envelope is transparent so that the imprinted information can be read prior to activating the fragrance release. During the wrapping process, an interior air filled void is created, which encloses both the card and a small quantity of air. The envelope is then hermetically sealed along its seams so that the fragrance compound is preserved until placed into service by a consumer. The film that forms the envelope has a vent opening formed through it, through which the fragrance disperses once placed into service. Prior to that time, an impermeable film vent closure is removably adhered to the envelope over the vent opening, which forms a substantially complete hermetic seal of the interior air filled void and the fragrance impregnated paperboard card. The vent closure has a pull tab so the consumer can readily remove the vent closure. Once the vent closure is removed, the fragrance compound begins to vaporize within the air filled void and disperses through the vent opening.

Reference is directed to FIG. 1, which is a perspective drawing of a fragrance impregnated wafer 2 according to an illustrative embodiment of the present invention. In the illustrative embodiment, the wafer 2 is a paperboard card, similar to what is known as blotter paper to those skilled in the art, that is semi-rigid and substantially planar. The card is approximately fifty millimeters by seventy-five millimeters, and approximately one-half millimeter thick. Other embodiments employ cards that are approximately fifty millimeters square, and fifty millimeters by sixty-seven millimeters. Those skilled in the art will appreciate that the exact size of the card is primarily a design choice. The exemplary illustrative embodiment, the fifty by seventy-five millimeter card will be discussed. On a first of the card's broad planar surfaces, there is printed a logotype, brand name, manufacturer identity and address, usage instructions and a usage warning. One the second broad planar surface, there may be printed a UPC barcode. The paperboard material is fibrous and porous, and therefore provides a particularly suitable physical carrier structure for a fragrance compound solution, consisting of fragrance components and a fragrance carrier solution. The card is impregnated with the fragrance compounds either prior to packaging, or during the packaging process. In certain illustrative embodiments, the card 2 is fully saturated, and in other embodiments, the card is impregnated with a lesser quantity of fragrance compound solution. The amount of solution utilized is a design choice based on the intended functional parameters of the product, such as the desired intensity of the fragrance release and the duration of effectiveness.

Figure 2:
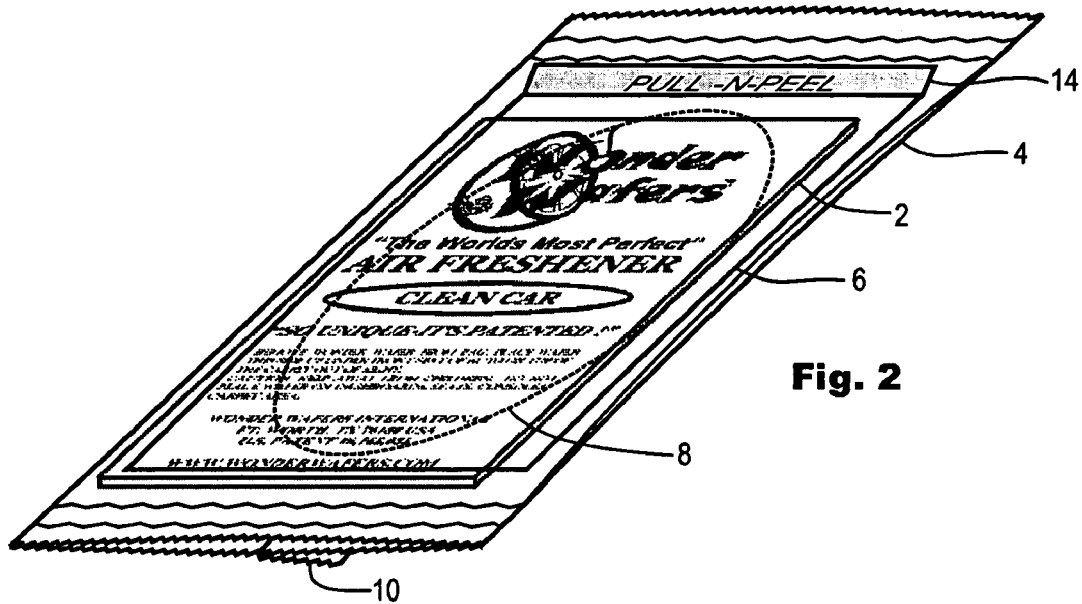
FIG. 2 is a drawing of a packaged fragrance impregnated wafer according to an illustrative embodiment of the present invention.

Reference is directed to FIG. 2, which is a drawing of a packaged fragrance impregnated wafer according to an illustrative embodiment of the present invention. The fragrance impregnated card 2 discussed with respect to FIG. 1 is illustrated in the packaging of the illustrative embodiment in FIG. 2. The package is an envelope 4 formed from an impermeable transparent film. The film is wrapped about the card 2, and is heat-sealed along a rear spine seam 10, as well as the two ends of the envelope 4. In the illustrative embodiment, impermeable means that the fragrance components and carrier solution components will not rapidly dissipate through the film, so as to provide a reasonable storage shelf life of the unopened product. The envelope 4 encloses and retains the card 2 therein. A vent opening 8 is formed through one side of the envelope 4. The vent opening 8, when exposed, allows the fragrance compounds dissipate there through and into the ambient environment, providing the intended delivery of the fragrance aromas. The vent opening 8 is sealed with a vent closure film 6, which is also impermeable to the fragrance compounds. The vent closure film 6 is sealably and removably adhered to the envelope 4 about the periphery of the vent opening 8, so as to provide a substantially complete hermetic seal of the envelope 4. A portion of the vent closure file film 6 is provided as a pull-tab 14, which is not adhered to the envelope 4, thusly enabling manual removable of the vent closure film 6 by the consumer.

The envelope 4 film and the vent closure 6 film serve to form the hermetic seal about the fragrance impregnated card 2. Since the card 2 is imprinted with useful information, is it beneficial for either the envelope 4 or the closure 6, or both, to be fabricated from a transparent material. This arrangement results in both the utilitarian advantage as well as a beneficial cost controlling measure. The same printed card stock that is used for bulk product sales can also be used for individually packaged product sales. And, the envelope and closure do not have to include or repeat the information imprinted on the card, or be of the same size and dimension. Several suitable film materials are available. Among these are polyethylene terephthalate polyester (commonly referred to as Mylar™), polypropylene film, and cellophane. Those skilled in the art will appreciate the advantages of each with respect to cost, durability, workability, and so forth.

Figure 3:
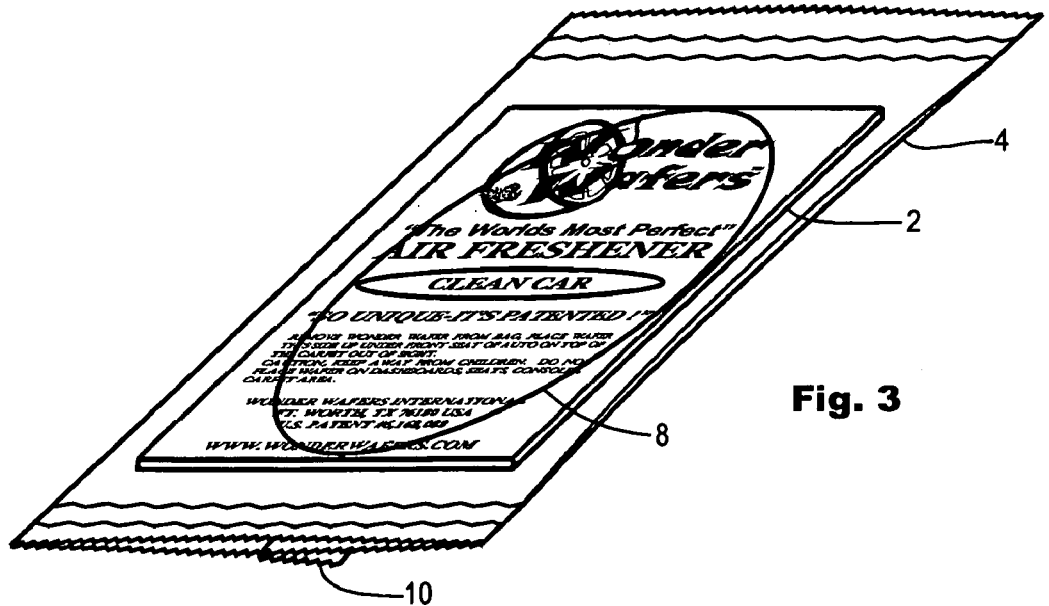
FIG. 3 is a drawing of a package fragrance impregnated wafer in use according to an illustrative embodiment of the present invention.

Reference is directed to FIG. 3, which is a drawing of a package fragrance impregnated wafer in use according to an illustrative embodiment of the present invention. FIG. 3 illustrates the same illustrative embodiment as FIG. 2, but with the vent closure 6 having been removed. In FIG. 3, the vent opening 8 is fully exposed, such that the ambient air can circulate about the fragrance impregnated card 4, also referred to more generally as the fragrance impregnated porous carrier. This interaction between the ambient air and the card 2 enables the fragrance compound to vaporize and then dissipate through the vent opening 8 of the envelope 4. Note that the envelope 4 is formed such that an air filled void remains inside the envelope after it is sealed. This enables the card 2 to move about within that air filled void, and enables the ambient air to circulate within the air filled void, thusly enhancing the vaporization and dissipation process.

Reference is directed to FIGS. 4A and 4B, which are front view and side view drawings of a fragrance impregnated wafer 2 according to an illustrative embodiment of the present invention. The proportions of the card 2 are presented, which is approximately fifty millimeters by seventy-five millimeters, by one-half millimeter in the illustrative embodiment. This yields a total surface area of approximately seventy-five hundred square millimeters, and a porous volume of approximately nineteen hundred cubic millimeters, which has proven to be an effective proportion for both the volume of fragrance compounds and rate of dissipation to sustain a fragrance release for several days. Those skilled in the art will appreciate that other shapes and volumes can be produced to yield similar results, or other results as may be desired for the intended market of the fragrance release product.

Reference is directed to FIG. 5, which is a drawing of a packaged fragrance impregnated wafer according to an illustrative embodiment of the present invention. The fragrance impregnated card 2 is positioned within the air filled void of the envelope 4, and behind the vent opening 8, which is sealed with the vent closure film 6. The envelope 4 is an impermeable film that is wrapped about the card 2. The film is heat sealed 12 near both ends of the envelope 4, as well as along a rear spine seal (not shown in FIG. 5). The vent closure film 6 is removably adhered to the envelope 4 about the periphery of the vent opening 8. In the illustrative embodiment, a pressure sensitive adhesive is used, as are known to those skilled in the art. In alternative embodiments, other removable adhesion techniques can be utilized, such as fusion, heat-sealing or other techniques known to those skilled in the art. In another particular embodiment, a resealable tacky adhesive is employed, which has the advantage of resealability so that the consumer can reseal the vent opening to stop and restart the release of fragrance from time to time, as desired. Suitable tacky adhesives are known to those skilled in the art. Note also in FIG. 5, that the envelope 4 size is somewhat larger than the card 2 size. In the illustrative embodiment, the envelope is approximately fifty percent, by area, larger than the card. This enables the card 2 to move about within an air filled void within the envelope 4. This arrangement also provides for less precision required in the manufacturing and alignment processes.

Reference is directed to FIG. 6, which is a drawing of a packaged fragrance impregnated wafer 2 placed in use according to an illustrative embodiment of the present invention. FIG. 6 presents the same embodiment as FIG. 5, except that the vent closure film 6 has been removed. In FIG. 6 the elliptically shaped vent opening 8 is illustrated, which providers access to the card 2 within the envelope 4 by ambient air. Note that the card 2 is positioned against the bottom and left sides of the air filled void of the envelope 4. At the same time, the upper right corner of the card 2 is still retained by the edge of the vent opening 8. This arrangement assures that the card remains within the envelope regardless of where it is positioned within the envelope. At the same time, it is desirable to have as large a vent opening 8 as can reasonable be achieved given the proportions of the envelope 4 and the card 2. In the illustrative embodiment, the elliptical vent opening is approximately the same size as the card (i.e. fifty millimeters by seventy-five millimeters), so the area of the vent opening is calculated as the area of an ellipse:

$$\text{Area} = \text{Pi} \times (\text{Width}/2) \times (\text{Length}/2) = 3.14 \times (50/2) \times (75/2) = 2945 \text{ mm}^2$$

The area of the card is calculated as:

$$\text{Area} = \text{Width} \times \text{Length} = 50 \times 75 = 3750 \text{ mm}^2$$

Thusly, the vent opening area is seventy-nine percent of the area of the card. It is desirable to keep the size of the vent opening to be a minimum of fifty percent of the area of one broad surface of the card. This enables good circulation within the air filled void and an adequately large aperture through which the fragrance components can dissipate.

Reference is directed to FIGS. 7A, 7B, and 7C, which are front view, side section view, and end section drawings, respectively, of a packaged fragrance impregnated wafer according to an illustrative embodiment of the present invention. The paperboard card wafer 2 is positioned within an air filled void created when the impermeable film is wrapped to form the envelope 4, which is then heat sealed along the spine seam 10 and heat sealed 12 at each end 12 before it is cut from a continuous roll of film during manufacture. The vent opening 8 and vent closure film 6 are indexed to align with the card placement and heat sealing operations. The vent closure film 6 is removably adhered to the envelope about the periphery of the vent opening 8. A "pull-n-peel" tab 14, which is not adhered to the envelope, is provided for manual removal of the vent closure by the consumer. The air filled void inside the envelope 4 is created by virtue of the envelop film, and the fact that the manufacturing process does not employ rollers or pressure plates that might squeeze the air out of the film as it is folded and sealed to create the envelope 4. In particular, the film has an elastic character which resists the creation of a hard crease line as it is folded. This holds the two broader surfaces of the envelope 4 away from one another, and creates the void into which the card 2 is position. The heat sealing operations 10 and 12 along the spine and near the ends 12 hermetically seal the card, the fragrance compound, and a small volume of air within the envelope. In this manner, the air filled void is preserved from the manufacturing process, through shipment and storage, and until such time as the consumer pulls the vent closure 6 from the vent opening 8.

Figure 8A:
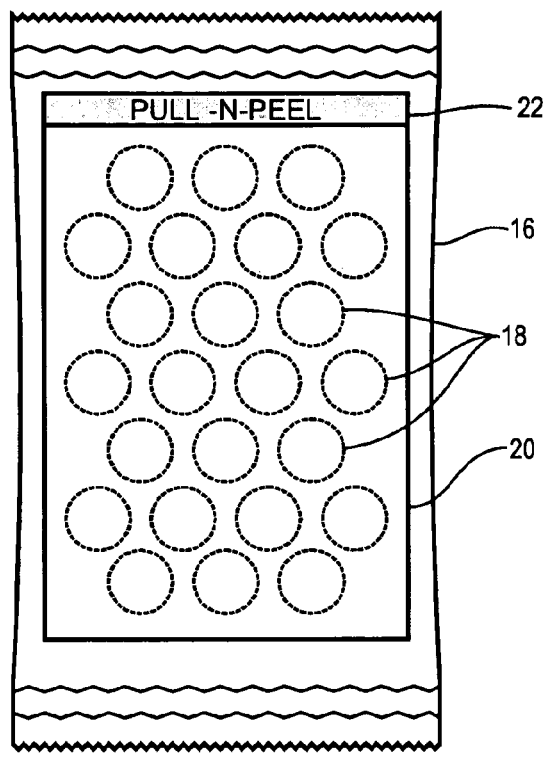
FIGS. 8A and 8B are drawings of a fragrance impregnated wafer package according to an illustrative embodiment of the present invention.
Figure 8B:
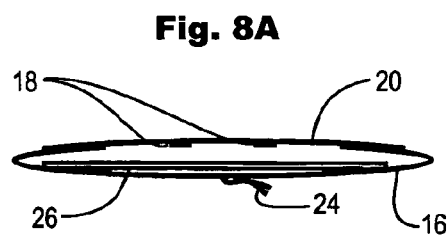

Reference is directed to FIGS. 8A and 8B, which are front view and end section view drawings, respectively, of a fragrance impregnated wafer package according to an illustrative embodiment of the present invention. The embodiment in FIG. 8 employs an envelope 16 similar to those previously discussed herein, which also includes a similar vent closure film 20 and pull-tab 22. The envelope 16 has a rear spine seam 24, and there is a fragrance impregnated porous carrier 26, as a paperboard card, placed in an air filled void within the envelope 16. Where the embodiment if FIG. 8 differs is in the use of plural individual apertures 18 to form the aforementioned vent opening for dispersion of the fragrance compound. In the illustrative embodiment, twenty-four holes are arranged in a staggered pattern, with each hole being twelve millimeters in diameter, which yields a total vent area of approximately twenty-seven hundred square millimeters. This result in a vent opening that is approximate seventy-two percent of the area of the aforementioned card size. Those skilled in the art will readily appreciated and any number of vent apertures could be combined to yield the desired minimum area of fifty percent as compared to one broad side of the porous fragrance carrier. Also, that the shape of each opening may be varied as desired to suit manufacturing needs, design factors, and matters of style. The two controlling limits are a total area of fifty percent minimum, and that the vent opening aperture, or apertures, retain the porous carrier within the air filled void of the envelop regardless of where the carrier may be located within the envelope.

Figure 9:
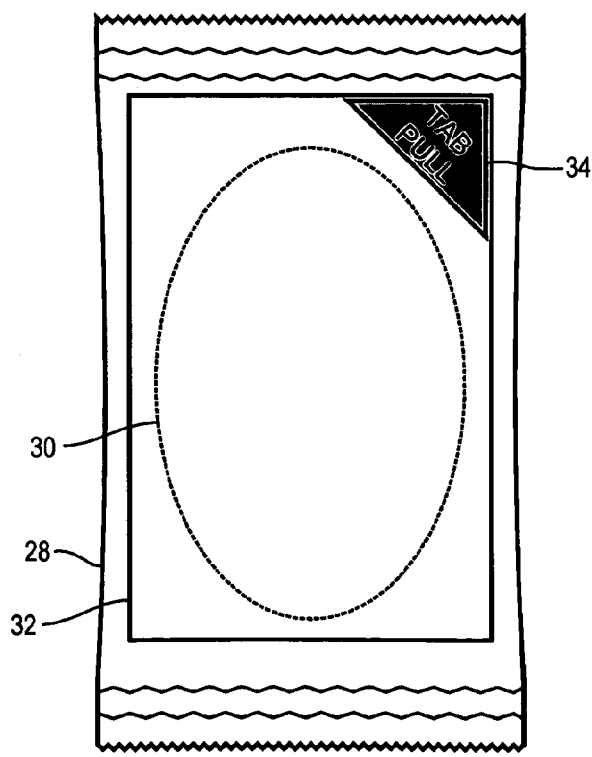
FIG. 9 is a drawing of a fragrance impregnated wafer package according to an illustrative embodiment of the present invention.

Reference is directed to FIG. 9, which is a drawing of a fragrance impregnated wafer package according to an illustrative embodiment of the present invention. The illustrative embodiment of FIG. 9 employs an impermeable film envelope 28 similar to those discussed hereinbefore. There is an vent opening 30 formed in the envelope, which is covered with an impermeable film vent closure 32. Where the embodiment in FIG. 9 principally differs is in the arrangement of the manual removal pull tab 34. In this embodiment, a corner portion of the vent closure 32 is not adhered to the envelope 28, and thusly is accessible for manual removable thereof by the consumer. Those skilled in the art will appreciate that any of a variety of pull tab configurations can readily be applied to achieve the objectives of the illustrative embodiments. Either a portion of the vent closure can omit the adhesion to the envelope, of an element can be added to the vent closure, which is otherwise manually accessible. What is necessary, is that the consumer have some portion accessible for manual removable of the vent closure by grasping and pulling, or otherwise removing, the vent closure from the envelope to expose the vent opening.

Figure 10A:
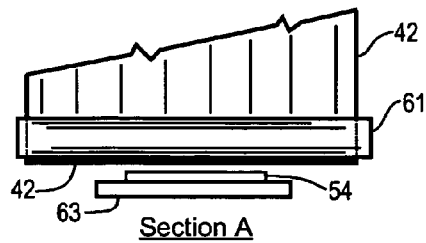
FIGS. 10 and 10A through 10D are drawings of a fragrance impregnated wafer packaging machine according to an illustrative embodiment of the present invention.
Figure 10B:
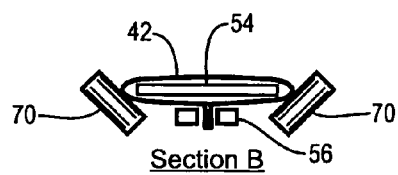
Figure 10C:
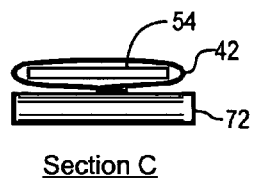
Figure 10D:
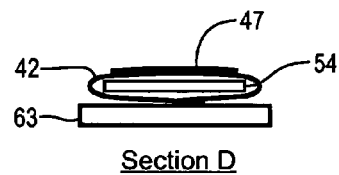
Figure 10:
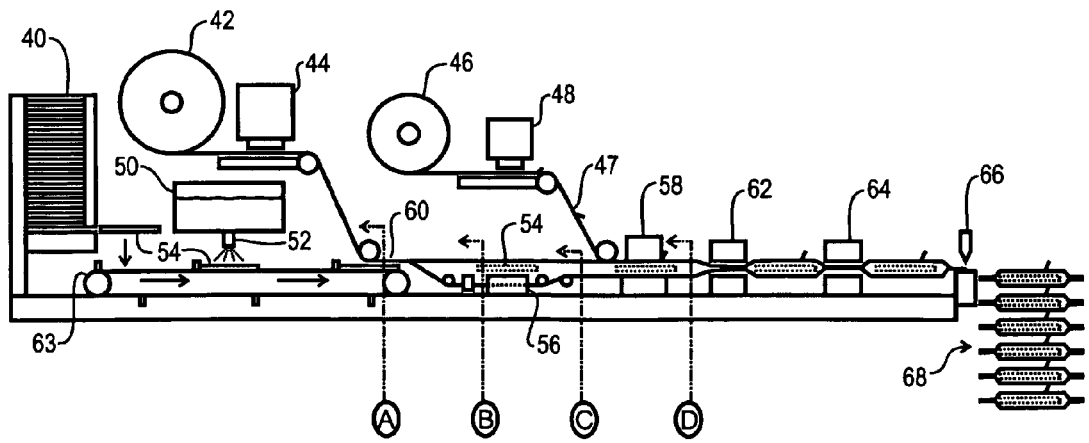

Reference is directed to FIGS. 10 and 10A through 10D, which are drawings of a fragrance impregnated wafer packaging machine, and related sectional views, according to an illustrative embodiment of the present invention. The object of the manufacturing process is to produce the packaged product for dispensing a fragrance compound at a low cost that has good storage characteristics and that is highly effective at delivering the fragrance at such time as it is pressed into service by the consumer. In FIG. 10, a plurality of paperboard cards 40 are inserted into a packaging machine. Individual cards 54 are transferred and fed through the assembly process by an indexed conveyor 63. In the illustrative embodiment, there are two ways in which the fragrance compounds are impregnated into the card, or porous carrier. The first method is to impregnate the cards with the fragrance compound prior to inserting them into the assembly machine 40. The second method is to apply the fragrance compound 50 to the individual cards 54 as they traverse the conveyor 63 by spraying, or applying by other suitable means, a predetermined quantity of fragrance compound to the individual cards 54. The impregnated cards then advance to station 60, where the impermeable film 42 is aligned with the individual cards 54. The film is payed out from a bulk roll of film 42 and fed by rollers to the conveyor 63, where it is aligned with the cards 54. The bulk film 42 may or may not already have the vent opening apertures formed there through, depending on how it is specified from the film supplier. In the case where the bulk film does not yet have the vent openings formed there through, then a vent opening punch machine 44 is added to the manufacturing process. In either case, the vent opening location in the bulk film is indexed to the location of the individual cards 54 as they traverse the conveyor 63. The techniques for achieving such index operations are known to those skilled in the art.

Section A illustrated in FIG. 10A is a view taken at station 60, where the film 42 is aligned with the card 54. Card 54 is resting on conveyor 63, and is aligned just above the card 54 by roller 61. Note that the width of the film 42 is more than twice as wide as the card, thereby provided adequate length to wrap the film 42 about the card 54 and form the aforementioned spine seal. In the illustrative embodiment, the film is approximately one hundred fifty millimeters wide. Now, continuing in FIG. 10, the card and film advance to station 56 where the film 42 is wrapped about the card 54 and the spine seal is fused using heat by heat fuser 56.

Section B illustrated in FIG. 10B is taken at station 56. A set of rollers 70 wrap the film 42 about the card 54 and form the spine seam in the film 42. The wrap is accomplished in a manner that avoids creating a hard crease in the edges of the folds. This action insures that an air filled void is created in the interior of the envelope that is formed. Heat sealer 56 fuses the spine seam on a continuous basis. Section C is illustrated in FIG. 10C, which is taken just aft of the heat sealer 56. Roller 72 folds the still warm spine seal in film 42 to one side. Again, note that there is an air filled void about card 54 within the wrapped film 42.

Now, continuing in FIG. 10, the vent closure film is provided on a bulk roll 46. The vent closure film has a pressure sensitive adhesive disposed on one side. The closure film 46 is payed out to a vent closure cutting tool 48, which forms the desired shape of the closure 47, as well as forms the manual pull tab portion. It will be appreciated by those skilled in the art that the envelope film 42 could be acquired from a supplier already punched with vent openings, and with the vent closure film adhered in place. Or, it may be acquired with the vent openings formed there through, but without the vent closures in place. Similarly, the vent closure film 46 may be acquired with the pull tabs already formed thereon. Or, each of these operations may be accomplished at the time of packaging the cards. These are design choices within the purview of those skilled in the art, and are primarily driven by cost considerations. In FIG. 10, the vent closure film 46, having been stamped individual vent closures with the pull tabs 47, are fed by rollers and aligned and indexed with the card 54 that have already been wrapped at station 58. At station 58, the vent closures 47 are pressed onto the enveloped film 42, and are thusly adhered into position.

Section D is illustrated in FIG. 10D, and shows the film enveloped 42 card 54 with the vent closure 47 in place, and resting on conveyor 63. Again, in FIG. 10, the running film, card, and vent closure envelope are closed and heat-sealed at stations 62 and 64, and then are finally cut into individual products 68 buy cutter 66.

Figure 11:
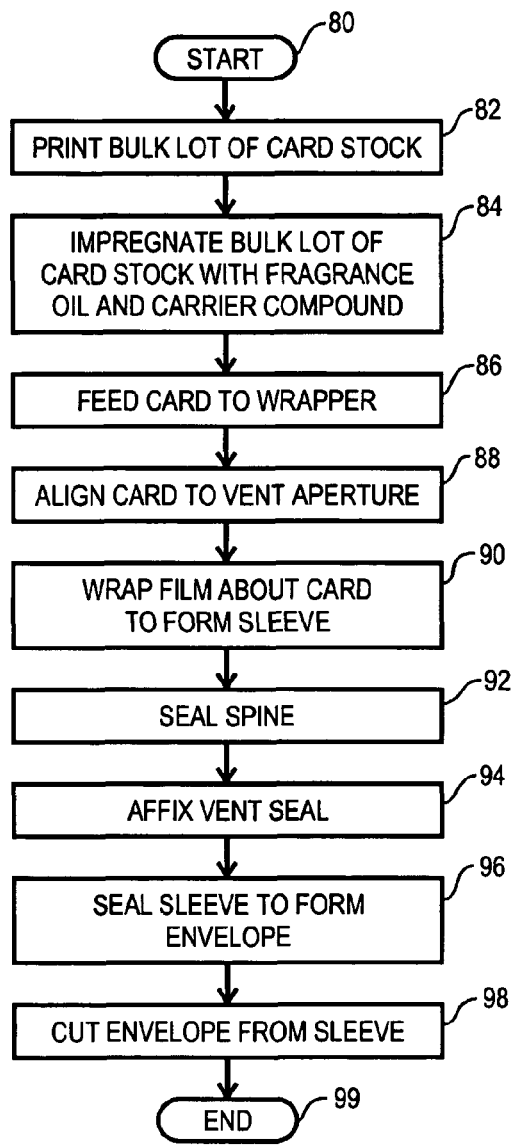
FIG. 11 is a manufacturing processing flow diagram according to an illustrative embodiment of the present invention.

Reference is directed to FIG. 11, which is a manufacturing processing flow diagram according to an illustrative embodiment of the present invention. The process in FIG. 11 generally corresponds to one version of the manufacturing embodiments that were described respecting FIG. 10. In FIG. 11, the process starts at step 80 and proceeds to step 82 where a bulk lot of card stock is printed with whatever imprint information is desired. At step 84, a bulk lot of cards are impregnated with fragrance compounds, such as fragrance oil and fragrance carrier solution. At step 86, the cards are inserted into the wrapping machine and are fed to the wrapping process. At step 88, the card is aligned to the vent opening aperture, and at step 90, the film is wrapped about the card. At step 92, the film spine seam is heat sealed. At step 94 the vent closure seal is aligned with the vent opening and is affixed to the envelope. At step 96, the ends of the envelope are sealed to form the hermetic seal about the card, and at step 98, the individual product is cut from the continuous envelope sleeve. The process ends at step 99.

Figure 12:
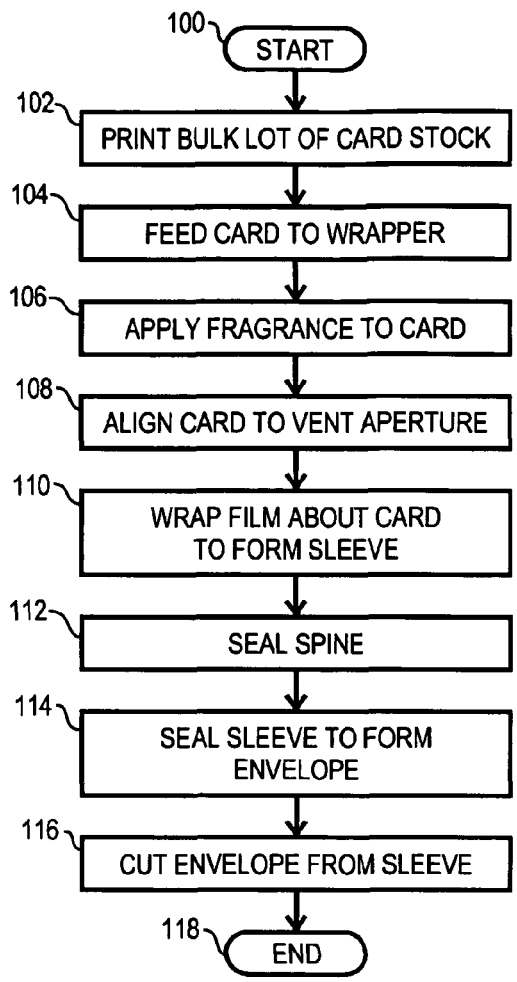
FIG. 12 is a manufacturing processing flow diagram according to an illustrative embodiment of the present invention.

Reference is directed to FIG. 12, which is another manufacturing processing flow diagram according to an illustrative embodiment of the present invention. The process in FIG. 12 generally corresponds to one other version of the manufacturing embodiments that were described respecting FIG. 10. In FIG. 12, The film is supplied from a supplier with the vent openings formed therein, and the vent closure film already applied to the vent openings. The process starts at step 100 and proceeds to step 102 where a bulk lot of card stock is printed with whatever imprint information is desired. At step 104, the cards are inserted into the wrapping machine and are fed to the wrapping process. At step 106, the fragrance compound is applied to individual cards as they traverse through the manufacturing process. At step 108, the card is aligned to the vent opening aperture, and at step 110, the film is wrapped about the card. At step 112, the film spine seam is heat sealed. At step 114, the ends of the envelope are sealed to form the hermetic seal about the card, and at step 116, the individual product is cut from the continuous envelope sleeve. The process ends at step 118.

Figure 13:
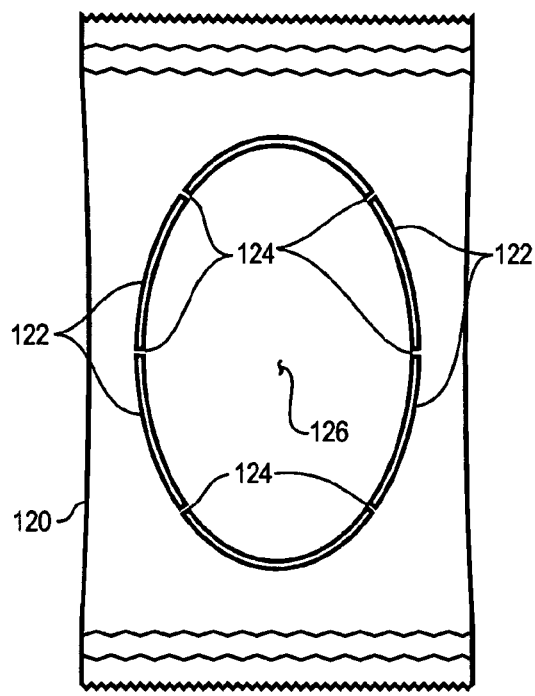
FIG. 13 is a drawing of a fragrance impregnated wafer package according to an illustrative embodiment of the present invention.

Reference is directed to FIG. 13, which is a drawing of a fragrance impregnated wafer package according to an illustrative embodiment of the present invention. During the manufacturing process of the aforementioned illustrative embodiments, the vent opening is formed in the envelope by cutting or punching away some material from the envelope. This creates waste material that is collected and disposed of during manufacturing. In the present embodiment, the vent opening waste material is not collected and disposed of during the manufacturing process. In the present embodiment, the vent opening is defined by punching or cutting one or more slits 122 in the envelope 120 film such that one or more tabs 124 of film material remain, which retain a vent opening removable portion 126 of the film in place over the vent opening. The fragrance compound impregnated porous carrier (not shown) is retained inside the envelope 120 in the same manner described hereinbefore.

Figure 14:
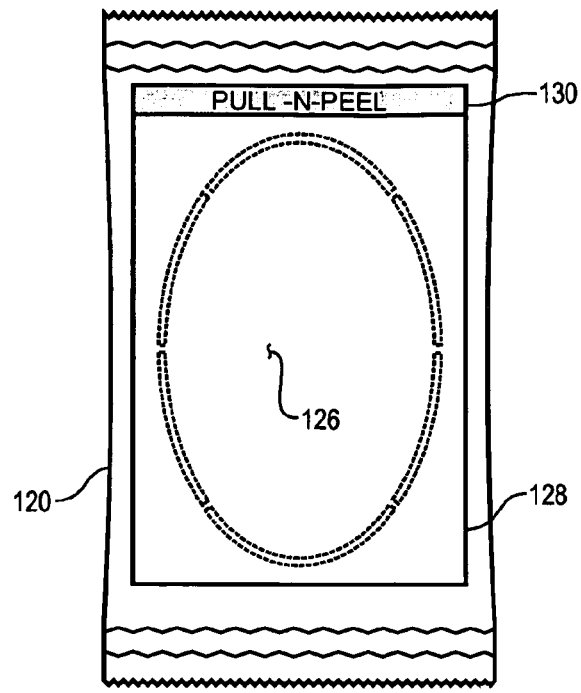
FIG. 14 is a drawing of a fragrance impregnated wafer package according to an illustrative embodiment of the present invention.

Reference is directed to FIG. 14, which is a drawing of a fragrance impregnated wafer package according to an illustrative embodiment of the present invention. In FIG. 14, the vent closure film 130 is adhered to the envelope 120 about the vent opening removable portion 126 of the envelope film so as to form a substantially complete hermetic seal within the envelope 120. A pull tab 130 is presented that is not adhered to the envelope 120 so as to enable manual removal of the vent closure film 128.

Figure 15:
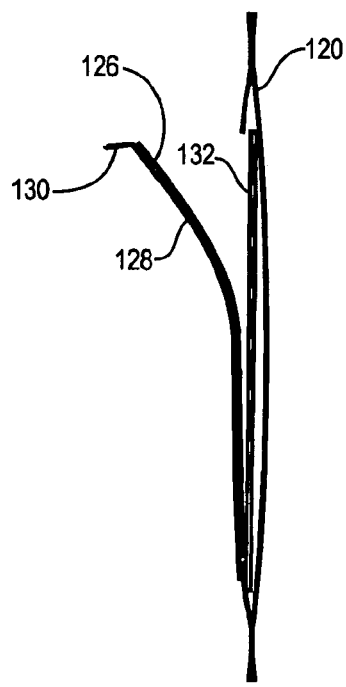
FIG. 15 is a section view drawing of a fragrance impregnated wafer package according to an illustrative embodiment of the present invention.

Reference is directed to FIG. 15, which is a section view drawing of a fragrance impregnated wafer package according to an illustrative embodiment of the present invention. FIG. 15 corresponds to FIG. 13 and FIG. 14. In FIG. 15, the fragrance impregnated porous carrier 132, which is a paperboard card in the illustrative embodiment, is illustrated within the envelope 120. The pull-tab 130 is used to draw the vent closure film 128 away from the envelope 120. Since the vent closure film 128 is adhesively attached to the envelope 120, the adhesive action pulls the vent opening removable portion 126 is drawn away from the envelope at the same time that the vent closure film 128 is drawn away.

Figure 16:
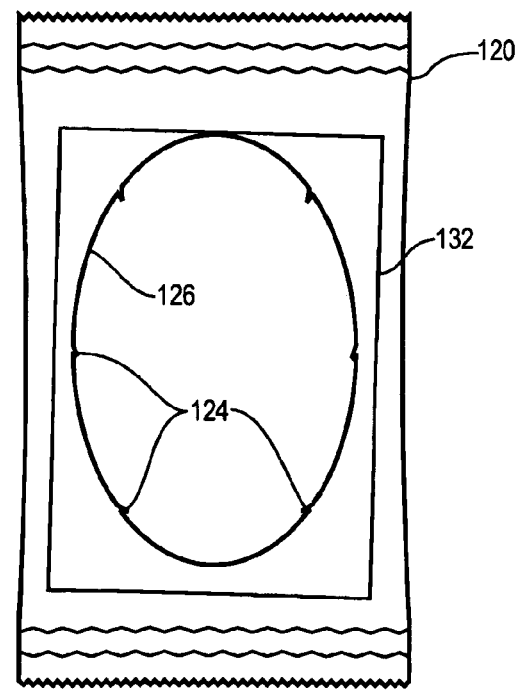
FIG. 16 is a drawing of a fragrance impregnated wafer package according to an illustrative embodiment of the present invention.

Reference is directed to FIG. 16, which is a drawing of a fragrance impregnated wafer package according to an illustrative embodiment of the present invention. FIG. 16 also corresponds to FIG. 13, FIG. 14 and FIG. 15. In FIG. 16, the envelope 120 is illustrated after the vent closure film (not shown) has been removed. The fragrance card 132 is illustrated within the envelope 120, now exposed through the vent opening 126. When the vent closure film (not shown) was pulled away, the vent opening removable portion (not shown) of the envelope was adhesively pulled away as well. This action causes the plural tabs 124 to tear, enabling the removable portion (not shown) to be disposed of together with the vent closure film (not shown).

Figure 17:
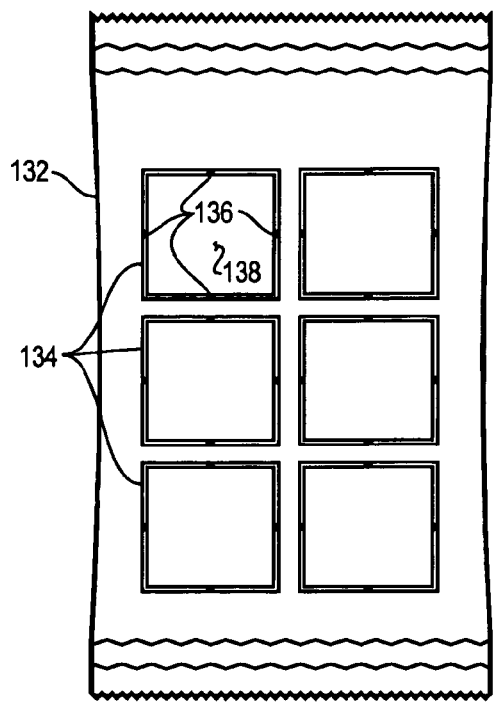
FIG. 17 is a drawing of a fragrance impregnated wafer package according to an illustrative embodiment of the present invention.
Figure 18:
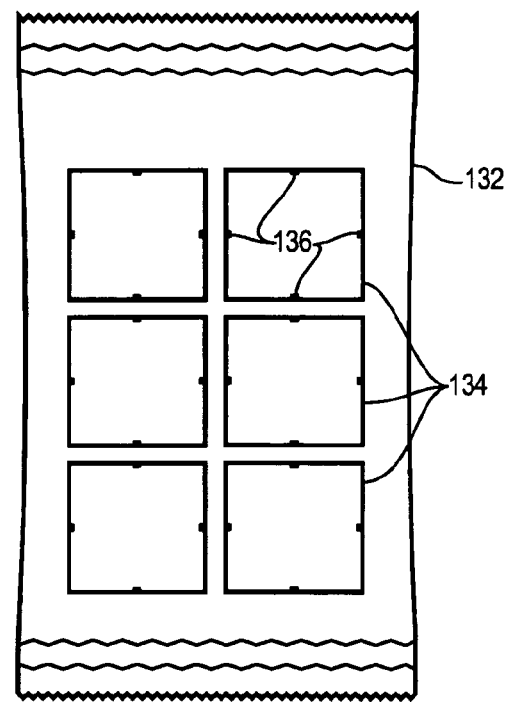
FIG. 18 is a drawing of a fragrance impregnated wafer package according to an illustrative embodiment of the present invention.

Reference is directed to FIG. 17 and FIG. 18, which are drawings of a fragrance impregnated wafer package according to an illustrative embodiment of the present invention. The embodiment presented illustrates an envelope 132 with plural square vent openings 134 defined using plural slits punched or cut into the envelope, and leaving plural tabs of film 136 to retain the vent opening removable portion 138 in place. When the vent closure (not shown) is removed, the removable portions 138 are pilled away and the plural tabs 136 are torn. This action presents plural vent openings 134 enabling dispersal of the fragrance there through.

Figure 19:
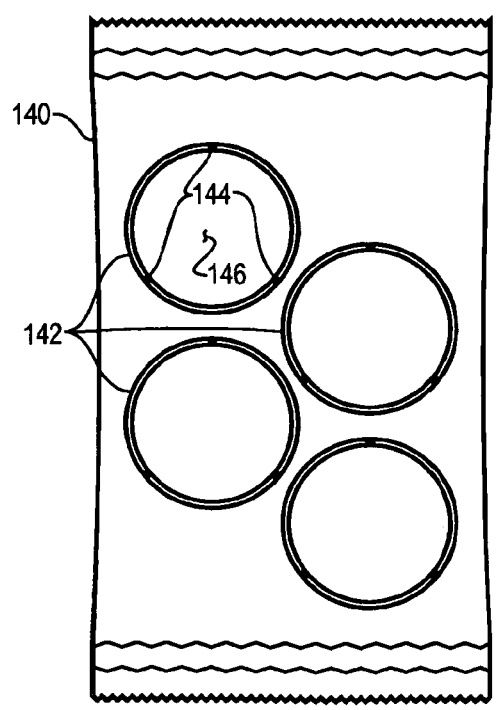
FIG. 19 is a drawing of a fragrance impregnated wafer package according to an illustrative embodiment of the present invention.
Figure 20:
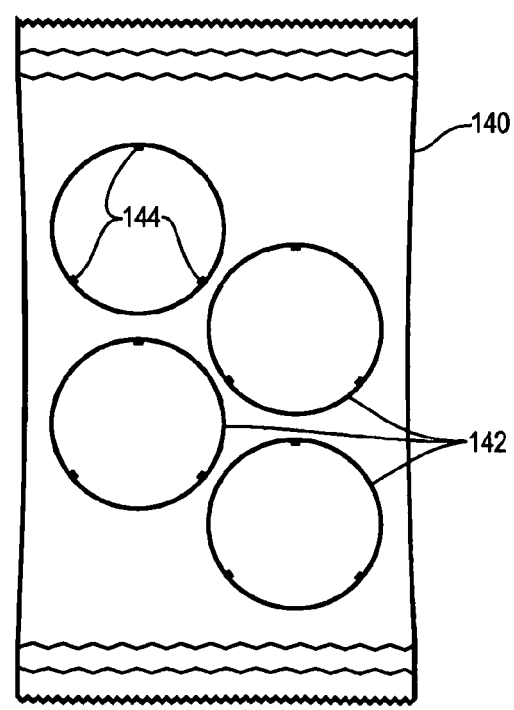
FIG. 20 is a drawing of a fragrance impregnated wafer package according to an illustrative embodiment of the present invention.

Reference is directed to FIG. 19 and FIG. 20, which are drawings of a fragrance impregnated wafer package according to an illustrative embodiment of the present invention. The embodiment presented illustrates an envelope 140 with plural round vent openings 142 defined using plural slits punched or cut into the envelope, and leaving plural tabs of film 144 to retain the vent opening removable portion 146 in place. When the vent closure (not shown) is removed, the removable portions 146 are pulled away and the plural tabs 144 are torn. This action presents plural vent openings 142 enabling dispersal of the fragrance there through.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. An apparatus for dispersing a fragrance compound, comprising:
   a fragrance compound impregnated porous carrier;
   a film wrapped about said porous carrier to form an envelope having an interior air filled void provided to enable said fragrance compounds to vaporize therein, and hermetically sealed along at least a first seam in said film, and wherein
   said film is perforated with plural slits to define a substantially complete vent opening and a vent opening removable portion that is retained to said envelope with plural tabs of film bridging said plural slits, and wherein said plural tabs of film constitute a tiny fraction of the total length of the perimeter of said vent opening;
   wherein said vent opening size and shape is selected to retain said porous carrier within said envelope regardless of where said porous carrier may be positioned within said air filled void, and such that the entire porous carrier is retained within the interior of said envelope;
   a film vent closure adhesively applied to said envelope about said vent opening removable portion, thereby forming a substantially complete hermetic seal of the interior of said envelope about said porous carrier, and wherein
   removal of said film vent closure adhesively pulls said vent opening removable portion from said envelope, such that said plural tabs of film are torn, to open said vent opening in said envelope, thereby enabling ambient air to circulate into said air filled void and further enabling said fragrance compound to vaporize into said air filled void and disperse from the interior of said envelope to the exterior through said vent opening and into the ambient environment, thereby dispersing vapors or said fragrance compound.

2. The apparatus of claim 1, and wherein said film is impervious to said fragrance compound.

3. The apparatus of claim 1, and wherein said porous carrier has information imprinted thereon, and wherein said film wrapped to form said envelop is transparent, thereby facilitating visual access to said information imprinted on said porous carrier.

4. The apparatus of claim 1, and wherein
said porous carrier has information imprinted thereon, and wherein
said film vent closure is transparent, thereby facilitating visual access to said information imprinted on said porous carrier.

5. The apparatus of claim 1, and wherein said film envelope and said film vent closure are polyester.

6. The apparatus of claim 1, and wherein said vent opening site and shape are selected to retain said porous carrier within said envelope regardless of where said porous carrier may be positioned within said envelope.

7. The apparatus of claim 1, and wherein
said film is perforated with plural slits to define plural vent opening removable portions, which are retained to said envelope with corresponding plural tabs of film.

8. The apparatus of claim 1, and wherein said porous carrier is a paperboard card.

9. The apparatus of claim 1, and wherein
said film, vent closure comprises a portion accessible for manual removal thereof from said envelope.

10. The apparatus of claim 9, and wherein
said portion accessible for manual removal is a pull tab that is not adhered to said envelope.

11. The apparatus of claim 1, and wherein said film vent closure is adhesively applied to said envelope with a resealable tacky adhesive.

12. The apparatus of claim 1, and wherein said film wrapped about said porous carrier to form said envelope is hermetically sealed along a spine seam, a first end seam and a second end seam.

13. A method of manufacturing an apparatus for dispersing a fragrance compound, comprising the steps of:
impregnating a porous carrier with a fragrance compound;
perforating a film with plural slits defining a substantially complete vent opening and vent opening removable portion that is retained with plural tabs of film bridging the plural slits, and wherein the plural tabs of film constitute a tiny fraction of the total length of the perimeter of the vent opening;
wrapping the film about the porous carrier, forming an envelope there about, having an air filled void for enabling the fragrance compound to vaporize therein;
sizing the vent opening for retaining the porous carrier within the envelope regardless of where the porous carrier is positioned within the air filled void, and such that the entire porous carrier is retained within the interior of the envelope;
hermetically sealing the envelope along at least a first scam in the film;
adhesively applying a film vent closure to the envelope about said vent opening removable portion, thereby forming a substantially complete hermetic seal of the interior of the envelope about said porous carrier, and
removing the film vent closure, thereby adhesively pulling the vent opening removable portion from the envelope and tearing the plural tabs of film, and thereby opening the vent opening in the envelope, and
thereby enabling ambient air to circulate into the air filled void enabling the fragrance compound to vaporize into the air filled void, and dispersing of the fragrance compound vapors from the interior of the envelope to the exterior through the vent opening and into the ambient environment, thereby dispersing vapors of the fragrance compound.

14. The method of claim 13, further comprising the step of: imprinting information onto the porous carrier.

15. The method of claim 14, and wherein the film that forms the envelope is transparent, thereby facilitating visual access to the information imprinted on the porous carrier.

16. The method of claim 14, and wherein the film vent closure is transparent, thereby facilitating visual access to said information imprinted on the porous carrier.

17. The method of claim 13, further comprising the steps of:
perforating the film with plural slits, thereby defining plural vent opening removable portions retained to the envelope with corresponding plural tabs of film.

18. The method of claim 13, further comprising the steps of: hermetically sealing the envelope along a spine seam, a first end seam and a second end seam.

* * * * *